United States Patent [19]

Agrawal

[11] 4,282,232
[45] Aug. 4, 1981

[54] NITROIMIDAZOLE RADIOSENSITIZERS FOR HYPOXIC TUMOR CELLS AND COMPOSITIONS THEREOF

[75] Inventor: Krishna C. Agrawal, New Orleans, La.

[73] Assignee: Research Corporation, New York, N.Y.

[21] Appl. No.: 33,513

[22] Filed: Apr. 26, 1979

[51] Int. Cl.³ ............... A61K 31/415; A61K 31/445; C07D 401/06; C07D 403/06
[52] U.S. Cl. ............................ 424/267; 424/273 R; 546/210; 548/336
[58] Field of Search ............ 546/210; 424/267, 273 R; 548/336

[56] References Cited

U.S. PATENT DOCUMENTS 3,646,057  2/1972  Beaman et al. .................. 546/210

OTHER PUBLICATIONS

Agrawal et al., "Abstract from the Joint Meeting of ASPET/SOT," Houston, TX, Aug. 13 to 17, 1978.
Beaman et al., "Antimicrobial Agents and Chemotherapy", p. 520, (1967).
Adams, "Chemotherapy", vol. 7, (1976), pp. 187–204.
Sheldon et al., "British Journal of Cancer", (1977) 35, p. 795.
Andrews, *The Radiobiology of Human Cancer Radiotherapy*, 2nd ed., (1978), University Park Press, pp. 471–505.

*Primary Examiner*—Henry R. Jiles
*Assistant Examiner*—R. W. Ramsuer
*Attorney, Agent, or Firm*—Oblon, Fisher, Spivak, McClelland & Maier

[57] ABSTRACT

Biologically active hypoxic cell radiosensitizers of the formula

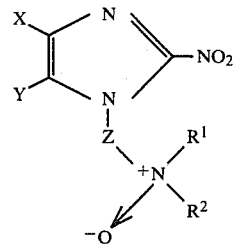

wherein Z is a $C_2$–$C_4$ alkylene group which may be substituted by OH; wherein $R^1$ and $R^2$ are same or different substituted or unsubstituted $C_1$–$C_4$ alkyl groups, or $R^1$ and $R^2$ taken together with the nitrogen atom form a heterocyclic ring of the formula

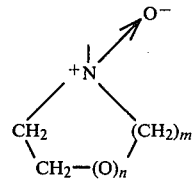

wherein
 n=0 or 1, with the condition that when n=0, m=2 or 3 and when n=1, m=1 or 2;
 X and Y are hydrogen, an electron withdrawing group or X and Y taken together form a six-membered carboxylic aromatic ring.

11 Claims, No Drawings

NITROIMIDAZOLE RADIOSENSITIZERS FOR HYPOXIC TUMOR CELLS AND COMPOSITIONS THEREOF

BACKGROUND OF THE INVENTION

Part of the work leading to this invention was funded by grant No. 2RolCA21050 from the National Cancer Institute, Department of Health, Education and Welfare of the United States. The U.S. Government is therefore granted a non-exclusive royalty-free license.

1. Field of the Invention

The present invention relates to novel nitroimidazole radiosensitizers useful for radiation therapy of tumor cells.

2. Description of the Prior Art

One of the most serious problems encountered during the X-ray radiotherapy of tumors is the relative resistance of hypoxic tumor cells to destruction. This radioresistance is directly related to the lack of oxygen in these cells, and X-ray doses have to be about three times higher to kill a given proportion of hypoxic cells than of well-oxygenated cells. Oxygen is the main radiosensitizer during X-ray therapy. The presence of hypoxic cells has been demonstrated repeatedly in animal tumors and results in resistance to radiation, which makes cures with a single dose of X-rays difficult or impossible. (Adams, G. E., et al, Chemotherapy, Vol. 7, p.187-206 (1976)). The resistance also is a serious limitation in attempts to increase the therapeutic ratio between tumor and normal tissue damage in radiotherapy. This disadvantage of hypoxic cells is reduced in tumors which can reoxygenate their hypoxic cells during fractionated radiotherapy, for example by shrinkage. It is probably reoxygenation during the course of radiation therapy which enables cures to be achieved at the present time.

To overcome the problem of hypoxia one proposed solution is to carry out radiation treatment of patients in high pressure oxygen (HPO) chambers. Although much experience has been gathered with this method, it is cumbersome and slow in its use. The shut-down of blood vessels is also a serious problem associated with this method.

Another solution to the problem of radiosensitization of hypoxic tumor cells, has been the use of fast neutron or negative $\pi$ meson radiation, rather than X-rays. Although neutrons are quite effective in tumors, the method is very expensive since it requires extensive facilities not readily available to most hospitals. Furthermore the OER (oxygen enhancement ratio) for neutrons or pions is only 1.5-1.7. The OER is the ratio of the slopes of the linear portions of the survival curves in the presence of radiosensitizer (or oxygen) compared to that in anoxia with no drug present. The higher the OER, the better will be the sensitizer approaching the effect of oxygen.

A third solution is the use of compounds which simulate oxygen in their ability to radiosensitize tumor cells. These compounds are provided externally and diffuse throughout the body. Because of this general distribution, it is important that they cause more damage to tumor cells than to normal tissue cells. Sensitization by DNA incorporating drugs, such as BUdR and FUdR (5-Bromodeoxyuridine and 5-Fluorodeoxyuridine) has been investigated, but the compounds failed precisely because of their poor selectivity problem. In 1963, Adams et al (Biophysic. Res. Comm., 12, 473 (1963)) proposed that the ability of compounds to sensitize hypoxic bacterial cells is directly related to their electron affinity. This idea has been generally verified and has aided the search for more active compounds. Nitrofurans for example are active in vitro for the radiosensitization of mammalian hypoxic cells. Since their metabolic half life is only a few minutes, however, they are not useful clinically (Chapman, J. D., et al, Cancel Research, 32, 2616 (1972)). Another compound which appeared promising in vitro but because of its chemical instability, has proven very limited for clinical trials is NDPP (p-nitro-3-dimethylamino propiophenone HCl) (Whitmore, G. F., et al, Rad. Res., 61, 325 (1975)).

Further searches for other drugs already in clinical use and posessing a chemical structure with electron-affinity, led to the discovery in 1973 of the radiosensitization action of metronidazole (I) by Foster and co-workers (Foster, J. L. and Wilson, R. L., Brit. J. Radiol., 46, 234 (1973)).

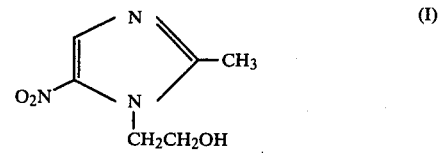

Metronidazole is active both in vivo and in vitro.

Another nitroimidazole radiosensitizer, misonidazole (II), has also recently proven to be of value (Asquith, J. D., et al, Rad. Res. 60, 108(1974)):

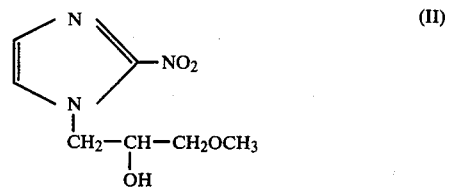

Both metronidazole and misonidazole are effective in vivo. However, both compounds show serious side effects when administered orally. They exhibit peripheral neuropathy and convulsions in mice and their central nervous system (CNS) toxicity is a limiting factor for their use in humans.

Therefore, a need continues to exist for a biologically active and clinically useful radiosensitizing compound, for the radiation treatments of tumor cells and which will show low CNS toxicity.

SUMMARY OF THE INVENTION

It is therefore an object of the invention to provide a radiosensitizing compound for the radiotherapy of tumor cells which is stable and biologically active. Another object of the invention is to provide a radiosensitizing compound for hypoxic tumor cells which shows low CNS toxicity. A further object of the invention is to provide a radiosensitizing compound of hypoxic tumor cells which has high electron affinity and which has decreased permeability through the blood brain barrier.

Still a further object of the invention is to provide a radio-sensitizing compound as described above, which contains an N-oxide functionality.

Still another object of the invention is to provide a process for preparing a radiosensitizing compound useful in the X-ray radiotherapy of tumor cells.

Yet another object of the invention is to provide pharmaceutically active compositions, useful in radiosensitization of hypoxic tumor cells. These and other objects of the invention which will readily become apparent hereinafter have been achieved by providing biologically active hypoxic cell radiosensitizing compounds having the formula (III):

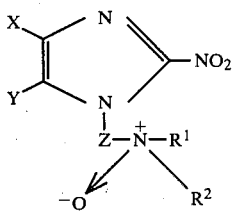
(III)

wherein Z is a $C_2$-$C_4$ alkylene group which may be substituted by —OH; $R^1$ and $R^2$ are the same or different substituted or unsubstituted $C_1$-$C_4$ alkyl groups or $R^1$ and $R^2$ taken together with the nitrogen atom form a heterocyclic ring of the formula:

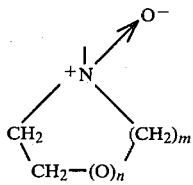

wherein n=0 or 1, on condition that when n=0, m=2 or 3 and when n=1, m=1 or 2; X and Y are hydrogen, an electron withdrawing group or X and Y taken together form a six membered carbocyclic aromatic ring.

Another object of the invention has been achieved by providing compositions which comprises a pharmaceutically active amount of a compound of the aforementioned formula III and a pharmaceutically acceptable inert carrier.

DESCRIPTION OF THE PREFERRED EMBODIMENTS

The principal feature of the present invention is to provide novel radiosensitizing compounds which contain both a nitroimidazole or nitrobenzimidazole functionality and also an N-oxide functionality. The nitroimidazole or nitrobenzimidazole structural characteristic of the compounds provide them with high electron affinity, essential for their use as hypoxic tumor cell radiosensitizers. The N-oxide functionality is related to their low CNS toxicity and therefore allows their extensive human clinical use. The addition of other electron-withdrawing groups enhances their electron affinity and thus their radiosensitization activity towards hypoxic tumor cells.

The compounds of the invention comprise those having the formula (III) (with their numbering system):

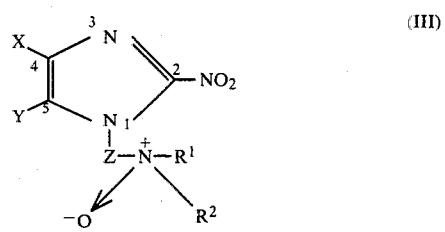
(III)

wherein Z is a $C_2$-$C_4$ alkylene group which may be substituted by —OH; $R^1$ and $R^2$ are the same or different substituted or unsubstituted $C_1$-$C_4$ alkyl groups or $R^1$ and $R^2$ taken together with the nitrogen atom form a heterocyclic ring of the formula:

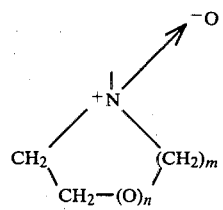

wherein n=0 or 1, on condition that when n=0, m=2 or 3 and when n=1, m=1 or 2;

X and Y are hydrogen or electron withdrawing substituents designed to enhance the final electron affinity of the compounds or X and Y taken together form a six membered carbocyclic aromatic ring.

X and Y electron withdrawing substituents useful in the present invention are nitro; acyl of the type $R^3CO$— where $R^3$=$C_1$-$C_4$ alkyl; nitrile; carboxyamide ($NH_2$—CO—); carboxyalkyl of the type $R^5O$—CO— wherein $R^5$ is $C_1$-$C_4$ alkyl; alkyloxime of the type $R^6$—N(O)=CH— wherein $R^6$ is $C_1$-$C_4$ alkyl; hydroxymethyl (HO—$CH_2$—); nitrilomethyl (NC—$CH_2$—); 2-phenylvinyl and 2-(nitrophenyl)vinyl.

As mentioned above, $R^1$ and $R^2$ may be substituted or unsubstituted $C_1$-$C_4$ alkyl groups. Substituents useful in this context are, for example, halides, such as F, Cl, Br, I; hydroxy; $C_1$-$C_4$ alkoxy; aryl, such as phenyl or naphtyl; nitrile; $C_1$-$C_4$ alkyl carboxy; formyl; carboxyamide and the like.

Preferred compounds are those wherein Z=—$CH_2$—$CH_2$—, wherein Y=$NO_2$; wherein X and Y form a benzene ring and wherein $R^1$ and $R^2$ together form a 6 membered ring which is substituted or unsubstituted with oxygen as part of the ring.

Specific preferred embodiments of the compounds of the present invention are 1-(1'-oxido)piperidinoethyl-2-nitroimidazole i.e., the compound of formula IVa:

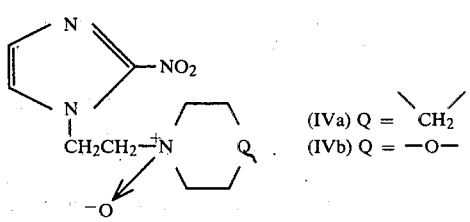

1-(1'oxido)morpholinoethyl-2-nitroimidazole (IVb)

1-(1'-oxido)piperidinoethyl-2-nitrobenzimidazole; i.e. compound Va

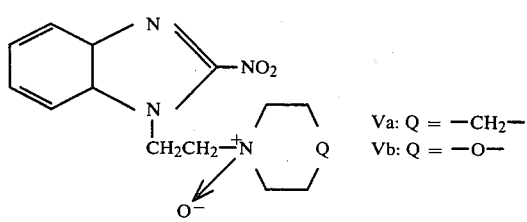

1-(1'-oxido) morpholinoethyl-2-nitrobenzimidazole; i.e., compound Vb (supra)

1-(1'-oxido)piperidinoethyl-2,4-dinitroimidazole
1-(1'-oxido)piperidoethyl-2,5-dinitroimidazole
1-(1'-oxido)morpholinoethyl-2,4-dinitroimidazole
1-(1'-oxido)morpholinoethyl-2,5-dinitroimidazole
1-(1'-oxido)piperidino-2''-hydroxypropyl-2-nitroimidazole
1-(1'-oxido)piperidino-2''-hydroxypropyl-2,4-dinitroimidazole
1-(1'-oxido)piperidino-2''-hydroxypropyl-2,5-dinitroimidazole The compounds of the present invention can be prepared by oxidizing the corresponding non-oxo derivatives VI with a mild oxidizing agent:

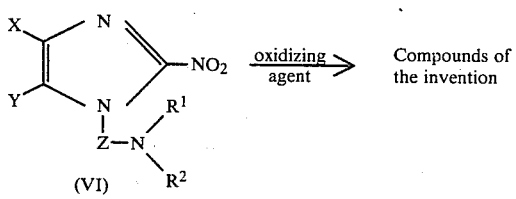

As a mild oxidation agent it is preferred to use metachloro perbenzoic acid (MCPBA), hydrogen peroxide ($H_2O_2$), peracids such as peracetic acid, $C_1$–$C_3$ alkylhydroperoxides, or the like. Preferably, M—CPBA, $H_2O_2$ or peracetic acid may be used, most preferably M—CPBA. The reaction is carried out either with or without a solvent at temperatures ranging from $-30°$ C. to $+200°$ C., depending on the reactivity of the starting amine-nitroimidazole derivative VI. Preferred solvents are alcohols, such as $C_1$–$C_{10}$ alcohols; halogenated hydrocarbons, such as chloroform, carbon tetrachloride, methylene chloride; $C_5$–$C_{10}$ aliphatic hydrocarbons, aromatic hydrocarbons, such as benzene, toluene, xylene; ethers, such as diethyl ether, diisopropyl ether, dimethyl ether, tetrahydrofuran, or the like; ketones, such as acetone; organic acids such as acetic acid or propionic acid; esters such as ethyl acetate; polar aprotic solvents such as dimethyl formamide, (DMF), dimethylsulfoxide (DMSO); acetonitrile and the like. Various mixtures with or without water may also be used. The times of reaction are 5 minutes to 12 hours, preferably 15 minutes to 3 hours. An excess of the oxidizing agent is preferably used such as, for example, a 100:1, most preferably a 10:1 molar excess over the starting amine. M—CPBA is preferably used in 1:1 molar ratio.

The amine-2-nitroimidazole starting materials VI can be prepared by standard nucleophilic reactions of the imidazole derivatives VII with amine-containing alkylating agents of formulae VIIIa or VIIIb:

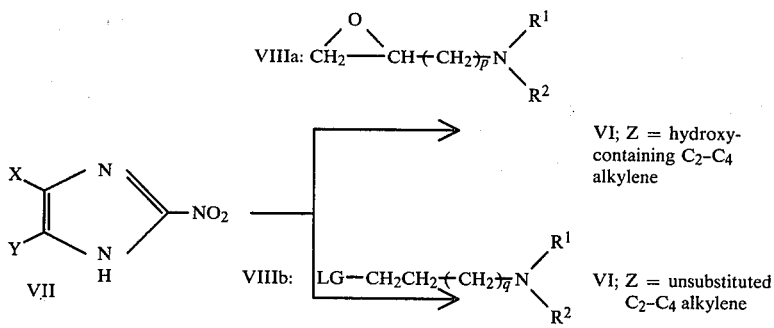

where p is 1 or 2 and q is 0, 1 or 2 and $R^1$, $R^2$, X and Y have the meanings described above.

Epoxides VIIIa are used when hydroxy-containing derivatives are desired and alkylating agents VIIIb are used when Z in formula VI is unsubstituted $C_2$–$C_4$ alkylene. In the alkylating agent VIIIb, LG is any leaving group capable of undergoing bimolecular nucleophilic ($SN_2$) substitution by the N-1 nitrogen atom of an imidazole ring. Preferably LG is a halide, such as —F, —Cl, —Br, —I; or a tosyl group or an acyl group. Most preferably LG is Cl or Br. The reaction is carried under conditions which maximize $SN_2$ reactivity, i.e., nonpolar aprotic solvents are preferred, such as dimethylsulfoxide, dimethylformamide, hexamethylphosphoric acid triamide, acetone, acetonitrile and the like. Reaction can also be carried out without solvent by heating VII directly with VIIIb.

A number of non-oxidized amine-containing nitroimidazoles of formula VI, as well as methods for their preparation, are disclosed in the following U.S. Patents, all of which are herein incorporated by reference:

Beaman et al, U.S. Pat. Nos. 3,646,057; 3,287,468 and 3,391,156
Giraldi et al, U.S. Pat. No. 3,399,193;
Pickholz et al, U.S. Pat. No. 3,417,091; and
Lancini et al, U.S. Pat. No. 3,420,842.

None of these references prepares N-oxides nor is there any discussion therein of using such N-oxides advantageously as radiosensitizers.

The preparation of substituted and unsubstituted nitroimidazoles VII may be carried out as follows:

1. 4(or 5)-acyl substituted 2-nitroimidazoles. These may be prepared by oxidization of the corresponding 4(5)-acyl substituted 2-aminoimidazoles with, for example, $NaNO_2/Cu$ under acidic conditions, or other such mild oxidizing agents. The 2-amino 4(5)-acylimidazoles can be prepared following the methods of Braun et al in J. Am. Chem. Soc., 150, 4208 (1978).

2. 2-nitro-benzimidazoles. These may be prepared by the general methodology of Beaman et al (Antimicrobial Agents & Chemotherapy, 469 (1965)) herein incorporated by reference.

3. 2,4(or 5)-dinitroimidazoles. These can be prepared by the general methodology of Agrawal, K. C., et al, J. Medicinal Chemistry, in press, 1979, which is herein incorporated by reference. Briefly, 2-nitroimidazole, prepared as described in (2) above can be further nitrated in the presence of an anhydride, with fuming $HNO_3$ to yield 2,4(or 5)-dinitroimidazoles. These compounds are also described in Lancini, G. C., et al, Farmaco. Ed. Sci., 18, 390 (1963).

4. Other substituted 2-nitroimidazoles. 2-nitroimidazoles substituted at position 4 or 5 with $C_1$-$C_4$ alkyl carboxy; nitrile, carboxyamide, $C_1$-$C_4$ alkyl oxime; hydroxymethyl; nitrilomethyl; 2-phenylvinyl or 2-(nitrophenyl)vinyl, may all be prepared from the common intermediate 2-nitro4(5)-formylimidazole (IX):

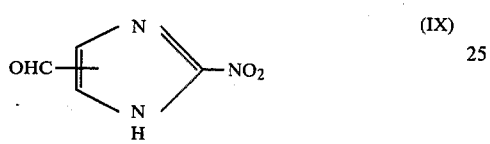

This formyl derivative, prepared by the methodology of Cavalleri et al (J. Heterocyclic Chem. 9, 979 (1972)), can be oxidized ($CrO_3$) and subsequently esterified to yield the alkylcarboxy derivative; it can be reduced ($NaBH_4$) to yield the hydroxymethyl derivative, which in turn can be chlorinated ($SOCl_2$) and further reacted with alkali metal cyanide (NaCN) to yield the nitrilomethyl derivative. The 4(5) formyl derivative IX can also be treated with $C_1$-$C_4$ alkyl hydroxylamines (alkylNH—OH) to yield $C_1$-$C_4$ alkyl oximes; it can be reacted with $NH_2OSO_3H$ to give the nitrile derivative, which in turn can be hydrated to yield a carboxamide derivative. The 2-phenylvinyl derivative or its nitrated analogue may be obtained as an intermediate in the aforementioned Cavalleri et al synthesis. All of the aforementioned single reactions are very well known to those in the art and details for their conditions and features can be readily ascertained without undue experimentation, by reference to standard textbooks in Organic Chemistry.

Both compounds VIIIa and VIIIb can normally be obtained commercially from Aldrich Chemical Corporation.

The present invention is based on the discovery that addition of an N-oxide functionality to nitro substituted imidazoles or benzimidazoles, not only retains the ability of the non-oxo parent compound to act as radio-sensitizers, but unexpectedly decreases their CNS toxicity and therefore enhances their clinical use. Without being bound by any particular theory, applicants speculate that the decreased CNS toxicity of the compounds of the present invention is due to their decreased permeability through the blood brain barrier. The decreased permeability is due to the ionic character of the compounds. However, it is clear that this cannot be the whole explanation since an ionic derivative such as 1-(1'-methiodide) piperidinoethyl-2-nitroimidazole (X), which contains a quaternary ammonium

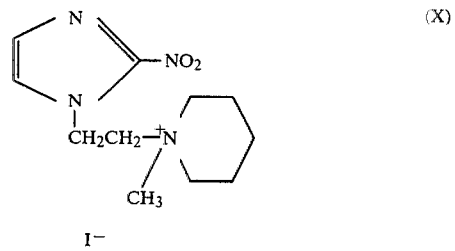

functionality is more toxic than the parent non-quaternized piperidino compound itself. The decreased CNS toxicity therefore is highly specific for the N-oxides and cannot simply be an "ionic effect". This decreased CNS toxicity yields unexpected and highly beneficial properties to the present compounds.

The dinitro derivatives are particularly useful since the present inventors have also presently discovered that the presence of two-nitro groups in imidazole derivatives of the formula (XI):

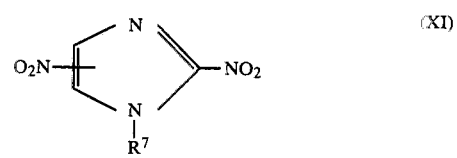

where $R^7$ is either H or —$CH_2$—$CH_2$—OH, yields radiosensitizing agents which have high efficiency yet moderate toxicity. Lowering the toxicity of these dinitro compounds further by addition of an N-oxide functionality therefore leads to preferred compounds in the present invention.

The compounds of this invention can be administered by any means that effects the radiosensitization of hypoxic tumor cells in patients undergoing X-ray radiotherapy. For example, administration can be parenterally, subcutaneously, intravenously, intramuscularly or intraperitoneally. Alternatively or concurrently, administration can be by the oral route. The dosage administered will be dependent upon the age, health and weight of the recipient, kind of concurrent treatment if any, frequency of treatment, and the nature of the effect desired. Generally, a dosage of active ingredient compounds will be from about 0.5 mg to 100 mg per kg of body weight. Normally, from 1 to 50 mg per kg per application, in one or more applications per radiotherapy is effective to obtain the desired result. The compounds can be employed in dosage forms such as tablets, capsules, powder packets, or liquid solutions, suspensions, or elixirs, for oral administration, or sterile liquid for formulations such as solutions or suspensions for parenteral use. In such compositions, the active ingredient will ordinarily always be present in an amount of at least 0.5% by weight based on the total weight of the composition and not more than 90% by weight. An inert, pharmaceutically acceptable carrier is preferably used.

Having now generally described this invention a more complete understanding can be obtained by reference to certain examples, which are included for purposes of illustration only and are not intended to be limiting unless otherwise specified.

I. CHEMICAL PREPARATIONS

Example I.1

Synthesis of 1-(1'-oxido)piperidinoethyl-2-nitroimidazole

The sodium salt of 2-nitroimidazole (0.01 mole) was reacted with a mixture of 0.01 mole of N-(2-chloroethyl)piperidine hydrochloride and 0.01 mole of sodium methoxide in 20 ml of xylene. The mixture was heated at 140° C. under reflux for 8 hours. The mixture was filtered, the filtrate was concentrated under vacuum. The residue was crystallized from a mixture of ethyl ether and hexane to yield 0.007 mole of 1-piperidinoethyl-2-nitroimidazole, m.p. 61°–62° C. The 1-piperidinoethyl-2-nitroimidazole (0.01 mole) was treated with 0.01 mole of m-chloroperbenzoic acid (m—CPBA) at room temperature for 30 minutes in 100 ml of chloroform as solvent. The resulting N-oxide was purified by recrystallization from chloroform and benzene, and had a m.p. of 108°–109° C. $^1$H-nmr: ($CD_3OD$) 7.12 and 7.47 (S, $C_{4,5}$-H),

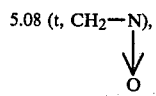

5.08 (t, $CH_2$—N), 3.60 (t, $NCH_2$) ppm. ir: (KBr) 1485 and 1360 ($NO_2$), 1270 $cm^{-1}$ (N→O).

Example I.2

Synthesis of 1-(1'-oxido)piperidinoethyl-2-nitrobenzimidazole

The sodium salt of 2-nitrobenzimidazole (0.01 mole) was reacted with 0.01 mole of N-(2-chloroethyl)piperidine in xylene at 140° C. for 4 hours in a similar manner as described above. The resulting 1-substituted piperidinoethyl derivative m.p. 61°–62° C. was reacted with equimolar quantity of m—CPBA at room temperature in 100 ml of chloroform as solvent for one hour to obtain the corresponding N-oxide in 70% yield, m.p. 105°–107° C. mp: ir: (KBr) 1490 and 1370 ($NO_2$), 1272 $cm^{-1}$ (N→O).

Example I.3

Preparation of 1-(1'-methiodide)piperidinoethyl-2-nitroimidazole

The 1-piperidinoethyl-2-nitroimidazole (1.0 gram, 0.0045 mole) prepared in Example I.1 was treated with 2 ml (0.032 mole) of $CH_3I$ at room temperature in 25 ml of ethanol as solvent. The mixture was stirred for 72 hours. The yellow precipitate yielded 1.65 grams of the quaternary methiodide (88% yield), m.p. 233°–234° dec.

II. BIOLOGICAL EXPERIMENTATION

II.I In vitro Cytotoxicity Experiments

Asynchronous monolayer cultures of Chinese hamster cells line V-79-753 B were employed in all the experiments. The monolayers were derived from exponentially-growing cultures. Methods of culturing and handling have been reported earlier by Cooke et al, Rad. Res. 65, 152 (1976). The plated cultures were rendered hypoxic in sealed dural containers capable of holding four petri dishes, by purging with nitrogen (oxygen-free grade) for one hour. Irradiation was carried out by using a Cobalt-60 source at a dose rate of approximately 310 rad/min according to the procedure described previously be Cooke et al, supra. A dose of 1395 rad was given to hypoxic cells in glass petri dishes in the presence of a given drug concentration (2000 cells/dish). Cell survival was estimated from unirradiated hypoxic cells exposed to the same drug concentration. Cultures were incubated for 6 days at 37° C. in an atmosphere of 5% $CO_2$; the resulting colonies were fixed in absolute ethanol, stained with methylene blue and counted.

To determine toxicity in vitro, glass petri dishes containing approximately 200 cells/dish were exposed to a range of concentrations of each drug for 2 hours at room temperature (20° C.) in air or in hypoxia. Drug concentrations between 10 μM were employed.

II.2 In vivo Neurotoxicity

Neurotoxicity in mice was determined using mice of strain $BDF_1$. This was carried out by (1) determining the $LD_{50}$ of each compound in mice and (2) observing the animals for acute neurotoxic symptoms such as convulsions. The drugs were either solubilized or suspended in normal saline and administered intraperitoneally to groups of 10 mice. The mice were observed for 24 hours for acute toxicity and death.

Table 1 shows the biological activity of selected N-oxides of the present invention, as well as comparisons with the corresponding non-oxides and the best radiosensitizers of the prior art, misonidazole and metronidazole:

TABLE 1

| Compounds (see legend) | A | B | C | D | E | F | G |
|---|---|---|---|---|---|---|---|
| Redox Potential | | | −0.32V | | | −0.389V | −0.486V |
| Radiosensitization (enhancement ratio at 1mM in chinese hamster cells) | | | 2.2 at 1mM | Approximately 2.1 at 1mM | | 2.2 at 1mM | 1.5 at 1mM |
| In-vitro Cytotoxicity in cells (2 hour exposure) | Nontoxic up to 10mM | 50% inhibition at 1mM | Nontoxic up to 20mM | 70% inhibition at 1mM | 30% inhibition at 2mM | | |
| Differential cytotoxicity of hypoxic cells | | | None up to 4 hours | | | yes | yes |
| Convulsions in mice at $LD_{50}$ doses | None | Yes | None | yes | yes | | |
| $LD_{50}$ in mice | ≃5g/kg | <1g | >5g/kg | 0.8g/kg | 0.25 g/kg | 1.6g/kg | 3.5g/kg* |

*P. W. Sheldon, et al, Br. J. Cancer, 35, 795, 800 (1977)

Compounds (A) 1-(1'-oxido)piperidinoethyl-2-nitrobenzimidazole
(B) 1-piperidinoethyl-2-nitrobenzimidazole (comparison)

(C) 1-(1'-oxido)piperidinoethyl-2-nitroimidazole
(D) 1-piperidinoethyl-2-nitroimidazole (comparison)
(E) 1-(1'-methiodide)-piperidinoethyl-2-nitroimidazole (comparison)
(F) Misonidazole
(G) Metronidazole As this data indicates, the N-oxide compounds of the present invention have toxicity and radiosensitization characteristics which make them ideal for use in radiotherapy treatments of humans. The non-oxide derivatives, known in the prior art as germicides, antiprotozoal agents or antiparasitic agents, are in fact also radiosensitizers. However, their toxicity in vivo and in vitro is high and renders them unsatisfactory for human uses. The oxide compounds prepared therefrom surprisingly have much lower toxicities and therefore represent a very useful addition to the art of radiosensitizers.

Having now fully described this invention, it will be apparent to one skilled in this art that many modifications and variations can be carried out without changing the scope or the nature thereof.

What is claimed as new and intended to be covered by Letters Patent is:

1. Biologically active hypoxic cell radiosensitizers of the formula

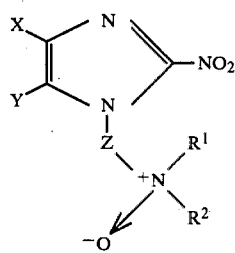

wherein Z is a $C_2$–$C_4$ alkylene group; wherein $R^1$ and $R^2$ taken together with the nitrogen atom form a heterocyclic ring of the formula

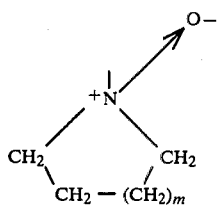

wherein
m=1 or 2;
X and Y are the same or different substituents selected from the group consisting of hydrogen, nitro; $R^3CO$— where $R^3$ is $C_1$–$C_4$ alkyl; nitrile, carboxyamide; $R^5OCO$— where $R^5$ is $C_1$–$C_4$ alkyl; $R^6$—N(O)=CH— where $R^6$ is $C_1$–$C_4$ alkyl; and nitrilomethyl.

2. The compounds of claim 1 wherein Z=—CH$_2$—CH$_2$—.

3. The compounds of claim 1 wherein $R^1$ and $R^2$ form a heterocyclic ring of the formula

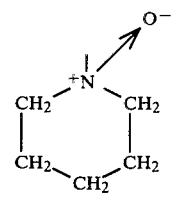

4. The compound of claim 1 which is 1-(1'-oxido)piperidinoethyl-2-nitroimidazole.
5. The compounds of claim 1 wherein either X or Y is nitro.
6. The compound of claim 1 which is 1-(1'-oxido)piperidinoethyl-2,4-dinitroimidazole.
7. The compound of claim 1 which is 1-(1'-oxido)piperidinoethyl-2,5-dinitroimidazole.
8. A composition useful for the radiosensitization of hypoxic tumor cells which comprises a pharmaceutically active amount of a compound having the formula:

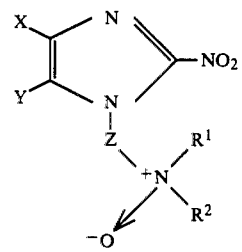

wherein Z is a $C_2$–$C_4$ alkylene group; wherein $R^1$ and $R^2$ taken together with the nitrogen atom form a heterocyclic ring of the formula

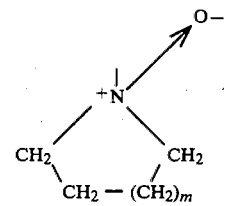

wherein
m=1 or 2;
X and Y are the same or different substituents selected from the group consisting of hydrogen, nitro; $R^3CO$— where $R^3$ is $C_1$–$C_4$ alkyl; nitrile; carboxyamide; $R^5OCO$— where $R^5$ is $C_1$–$C_4$ alkyl; $R^6$—N(O)=CH— wherein $R^6$ is $C_1$–$C_4$ alkyl; and nitrilomethyl; and an inert pharmaceutically acceptable carrier.

9. The composition of claim 8 wherein Z=—CH$_2$CH$_2$—.
10. The composition of claim 8 wherein X or Y is nitro.
11. The composition of claim 8 wherein $R^1$ and $R^2$ taken together form a heterocyclic ring of the formula:

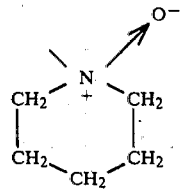

* * * * *

UNITED STATES PATENT AND TRADEMARK OFFICE
CERTIFICATE OF CORRECTION

PATENT NO. : 4,282,232

DATED : August 4, 1981

INVENTOR(S) : K.C. AGRAWAL ET AL

It is certified that error appears in the above—identified patent and that said Letters Patent is hereby corrected as shown below:

In the Abstract, last line, please delete "carboxylic" and replace therefore --carbocyclic--;

Column 10, line 31, please delete "between 10µM" and replace therefore --as shown in Table 1"--.

Signed and Sealed this

Thirtieth Day of March 1982

[SEAL]

Attest:

Attesting Officer

GERALD J. MOSSINGHOFF

Commissioner of Patents and Trademarks